United States Patent
Klug et al.

(10) Patent No.: US 8,338,483 B2
(45) Date of Patent: Dec. 25, 2012

(54) METHOD FOR PRODUCING ACYLGLYCINATES

(75) Inventors: Peter Klug, Grossostheim (DE); Franz-Xaver Scherl, Burgkirchen (DE)

(73) Assignee: Clariant Finance (BVI) Limited, Tortola (VG)

( * ) Notice: Subject to any disclaimer, the term of this patent is extended or adjusted under 35 U.S.C. 154(b) by 116 days.

(21) Appl. No.: 12/743,458

(22) PCT Filed: Nov. 14, 2008

(86) PCT No.: PCT/EP2008/009646
§ 371 (c)(1),
(2), (4) Date: May 28, 2010

(87) PCT Pub. No.: WO2009/065530
PCT Pub. Date: May 28, 2009

(65) Prior Publication Data
US 2010/0273879 A1    Oct. 28, 2010

(30) Foreign Application Priority Data

Nov. 20, 2007 (DE) .......................... 10 2007 055 265

(51) Int. Cl.
*A61K 31/198* (2006.01)
*C07C 229/00* (2006.01)

(52) U.S. Cl. ....................... 514/563; 554/110

(58) Field of Classification Search .............. None
See application file for complete search history.

(56) References Cited

U.S. PATENT DOCUMENTS

| | | | |
|---|---|---|---|
| 6,703,517 B2 | 3/2004 | Hattori et al. | |
| 6,828,452 B2 | 12/2004 | Raths et al. | |
| 2001/0002257 A1* | 5/2001 | Stolz ............................ | 424/401 |
| 2005/0085651 A1 | 4/2005 | Kitamura et al. | |
| 2007/0232508 A1 | 10/2007 | Oshimura | |
| 2010/0286418 A1 | 11/2010 | Klug et al. | |
| 2010/0305358 A1 | 12/2010 | Klug et al. | |

FOREIGN PATENT DOCUMENTS

| | | |
|---|---|---|
| EP | 0648833 | 4/1995 |
| EP | 1314717 | 5/2003 |
| EP | 1672055 | 6/2006 |
| JP | 8053693 | 2/1996 |
| JP | 11 246473 | 9/1999 |
| WO | WO96/39375 | 12/1996 |
| WO | WO02/057217 | 7/2002 |
| WO | WO2008000648 | 1/2008 |
| WO | WO2008000671 | 1/2008 |
| WO | WO 2008019807 | 2/2008 |

OTHER PUBLICATIONS

Gervajio, Bailey's Industrial Oil and Fat Products, Fatty Acids and Derivatives From Coconut Oil, 6th Edition, 2005, John Wiley & Sons, Inc., pp. 1-56.*
International Search Report for PCT/EP2007/007128.
Translation of International Preliminary Examination Report for PCT/EP2007/007128.
L. Prati, G. Martra, Gold Bull. 39 (1999) 96.
L. Prati, F. Porta, Applied catalysis A: General 291 (2005) 199-203.
S. Biella, G.L. Castiglioni, C. Fumagalli, L. Prati, M. Rossi, Catalysis Today 72 (2002) 43-49.
International Search Report for PCT/EP2008/009646.
Translation of International Preliminary Examination Report for PCT/EP2008/009646.
International Search Report for PCT/EP2009/000034.
Translation of International Preliminary Examination Report for PCT/EP2009/000034.
English Abstract for JP 11 246473, 1999.
English Abstract for JP 8053693, 1996.
Choji Kashima et al: "Amino alcohols as C-terminal protecting groups in peptide synthesis" J. Chem Soc. Perkin Trans I, vol. 3 1988, pp. 535-539.

* cited by examiner

*Primary Examiner* — Paul A Zucker
(74) *Attorney, Agent, or Firm* — Tod A. Waldrop

(57) ABSTRACT

The invention relates to a method for producing acylglycinates of formula (I)

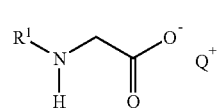

Formula (I)

wherein $R^1$ represents a linear or branched, saturated alkanoyl group having between 6 and 30 carbon atoms, or a linear or branched, mono- or polyunsaturated alkenoyl group having between 6 and 30 carbon atoms, and $Q^+$ represents a cation selected from the alkali metals $Li^+$, $Na^+$ and $K^+$, characterised in that glycine comprises fatty acid chloride $R^1Cl$, wherein $R^1$ which has the meaning given in formula (I), is provided in water and in presence of a basic alkali compound, the cations $Q^+$ are selected from $Li^+$, $Na^+$ and $K^+$, but in the absence of organic solvents, is reacted at between 30-35 DEG C, and the proportion of fatty acid chloride $R^1Cl$ containing acyl groups $R^1$ having 18 or more carbon atoms, in relation to the total amount of used fatty acid chloride, is less than 2.0% in wt.

12 Claims, No Drawings

METHOD FOR PRODUCING ACYLGLYCINATES

Method for producing acylglycinates

The invention relates to a method for producing acylglycinates and compositions containing acylglycinates.

Acylglycinates of the formula (Ia)

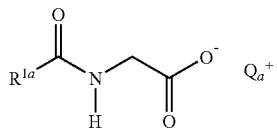

Formula (Ia)

in which
$R^{1a}$—C(O) is a linear or branched, saturated alkanoyl group having 6 to 30, preferably 8 to 22, particularly preferably 8 to 18, carbon atoms or is a linear or branched, mono- or polyunsaturated alkanoyl group having 6 to 30, preferably 8 to 22 and particularly preferably 12 to 18 carbon atoms, and
$Q_a^+$ is a cation selected from the alkali metals $Li^+$, $Na^+$, $K^+$, the alkaline earth metals $Mg^{++}$, $Ca^{++}$, but is also $Al^{+++}$ and/or $NH_4^+$, a monoalkylammonium, dialkylammonium, trialkylammonium and/or tetraalkylammonium ion, it being possible for the alkyl substituents of the amines, independently of one another, to be $(C_1-C_{22})$-alkyl radicals or $(C_2-C_{10})$-hydroxyalkyl radicals,
are surfactants which are valued, particularly in cosmetics, for face cleansing formulations in Asia in skin cleansing products. This applies in particular to sodium and potassium cocoylglycinate.

The surfactants, in particular the sodium and the potassium cocoyl-glycinate, foam in an excellent manner in slightly alkaline solution and produce a pleasant, non-oily feeling on the skin.

In contrast to the corresponding N-methylglycine derivatives, the so-called sarcosinates, glycinates, however, have problematic properties in the preparation. As described in JP 8053693, acylglycinates can be obtained in water without additional solvents only in purities of just above 90% and form very highly viscous reaction solutions in the Schotten-Baumann reaction. As a result of this high viscosity, the hydrolysis of the fatty acid chloride used for the preparation is promoted and leads to reduced purity of the acylglycinate. JP 8053693 therefore proposes the addition of alcohols, such as isopropanol, isobutanol or tert-butanol, in the preparation of acylglycinates.

However, owing to the odor of the alcohols, this procedure is not advantageous, and it is for this reason that the alcohols are removed again from the reaction mixture also after acidification and phase separation and the desired alkanoylglycinate is generally obtained as a quality having a low salt content after neutralization. This method is complicated and gives rise to sodium chloride-containing wastewaters which have to be disposed of.

It was therefore the object to provide a method for producing acylglycinates or compositions containing acylglycinates, which process does not have the abovementioned disadvantages or at least alleviates these disadvantages and in particular has the advantage that it can be effected without use of organic solvents and gives acylglycinates of high purity. The method should also permit the direct preparation of compositions having a high active content of acylglycinate and having low viscosities.

Surprisingly, it was found that this object is achieved if the acylglycinates are prepared by reacting glycine with fatty acid chloride in water and in the presence of a basic alkali metal compound but in the absence of organic solvents, the preparation of the acylglycinates is carried out at a temperature of 30-35° C. and the proportion of fatty acid chloride containing acyl groups having 18 or more carbon atoms, based on the total amount of fatty acid chloride used, is less than 2.0% by weight.

The invention therefore relates to a method for producing acylglycinates of the formula (I)

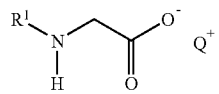

Formula (I)

in which
$R^1$ is a linear or branched, saturated alkanoyl group having 6 to 30, preferably 8 to 22 and particularly preferably 8 to 18 carbon atoms or is a linear or branched, mono- or polyunsaturated alkenoyl group having 6 to 30, preferably 8 to 22 and particularly preferably 12 to 18 carbon atoms, and
$Q^+$ is a cation selected from the alkali metal cations $Li^+$, $Na^+$ and $K^+$, preferably selected from $Na^+$ and $K^+$ and particularly preferably is $Na^+$,
wherein glycine is reacted with fatty acid chloride $R^1Cl$, $R^1$ having the meaning stated in formula (I), in water and in the presence of a basic alkali metal compound which provides cations $Q^+$ selected from $Li^+$, $Na^+$ and $K^+$, preferably selected from $Na^+$ and $K^+$ and particularly preferably $Na^+$, but in the absence of organic solvents, at 30-35° C., and the proportion of fatty acid chloride $R^1Cl$ containing acyl groups $R^1$ having 18 or more carbon atoms, based on the total amount of fatty acid chloride used, is less than 2.0% by weight.

In the present invention, the linear or branched, saturated alkanoyl groups $R^1$ from formula (I) and the linear or branched, mono- or polyunsaturated alkenoyl groups $R^1$ from formula (I) are also together designated as "acyl groups".

The fatty acid chlorides used in the method according to the invention and having a low proportion of long-chain acyl groups can be obtained by methods known to the person skilled in the art, for example by distillation from customary fatty acid chlorides.

Carbonates or hydroxides, preferably hydroxides, of the alkali metal cations $Li^+$, $Na^+$ or $K^+$ or mixtures thereof are preferably used as basic alkali metal compounds. NaOH and/or KOH are particularly preferred, NaOH being especially preferred.

The method according to the invention is preferably carried out at a pH of from 9 to 13, particularly preferably from 12 to 13.

Furthermore, the method according to the invention is preferably carried out in such a way that glycine and fatty acid chloride are used in equimolar amounts. Particularly preferably, the fatty acid chloride is used in slightly less than the stoichiometric amount, based on glycine. The molar ratio of glycine to fatty acid chloride $R^1Cl$ is particularly preferably from 1.1:1.0 to 1.0:1.0 and extremely preferably from 1.05:1.0 to 1.0:1.0.

In a further preferred embodiment of the method according to the invention, fatty acid chlorides $R^1Cl$ containing acyl groups $R^1$ having 8 to 18 carbon atoms, the proportion of fatty acid chloride $R^1Cl$ containing acyl groups $R^1$ having 18 carbon atoms, based on the total amount of fatty acid chloride $R^1Cl$ used, being less than 2.0% by weight, are reacted in the presence of a basic alkali metal compound which provides cations $Q^+$ selected from $Li^+$, $Na^+$ and $K^+$, preferably selected from $Na^+$ and $K^+$ and particularly preferably $Na^+$. The basic alkali metal compounds are preferably carbonates or hydroxides, preferably hydroxides, of the alkali metal cations $Li^+$, $Na^+$ or $K^+$ or mixtures thereof, particularly preferably NaOH or KOH and especially preferably NaOH.

In a further preferred embodiment of the method according to the invention, $C_{8-18}$-fatty acid chlorides, preferably cocoyl chlorides, which contain a proportion of fatty acid chloride having $C_{18}$-acyl groups of less than 2.0% by weight, based on the total amount of fatty acid chloride used, are reacted in the presence of a basic alkali metal compound which provides cations $Q^+$ selected from $Li^+$, $Na^+$ and $K^+$, preferably selected from $Na^+$ and $K^+$ and particularly preferably $Na^+$. The basic alkali metal compounds are preferably carbonates or hydroxides, preferably hydroxides, of the alkali metal cations $Li^+$, $Na^+$ or $K^+$ or mixtures thereof, particularly preferably NaOH or KOH and especially preferably NaOH.

In a particularly preferred embodiment of the method according to the invention, cocoyl chlorides having $C_{8-18}$-acyl groups, the proportion of fatty acid chlorides having $C_{18}$-acyl groups, based on the total amount of cocoyl chloride used, being less than 2.0 and preferably less than 1.0% by weight, are reacted in the presence of a basic alkali metal compound which provides $Na^+$ cations. The basic alkali metal compounds are preferably $Na_2CO_3$ or NaOH and particularly preferably NaOH.

In a particularly preferred embodiment of the method according to the invention, cocoyl chlorides having $C_{8-18}$-acyl groups, the proportion of fatty acid chlorides having $C_8$- and $C_{10}$-acyl groups together being greater than 5.0% by weight, preferably from 10.0 to 14.0% by weight, the proportion of fatty acid chlorides having $C_{12}$-acyl groups from 50.0 to 7.20% by weight and the proportion of fatty acid chlorides having $C_{18}$-acyl groups less than 2.0 and preferably less than 1.0% by weight, based in each case on the total amount of cocoyl chloride used, are reacted in the presence of a basic alkali metal compound which provides $Na^+$ cations. The basic alkali metal compounds are preferably $Na_2CO_3$ or NaOH and particularly preferably NaOH.

In a further preferred embodiment of the method according to the invention, fatty acid chloride $R^1Cl$, in which $R^1$ is an acyl group having 12 carbon atoms, are reacted in the presence of a basic alkali metal compound which provides cations $Q^+$ selected from $Li^+$, $Na^+$ and $K^+$, preferably selected from $Na^+$ and $K^+$ and particularly preferably $Na^+$. The basic alkali metal compounds are preferably carbonates or hydroxides, preferably hydroxides, of the alkali metal cations $Li^+$, $Na^+$ or $K^+$ or mixtures thereof, particularly preferably NaOH or KOH and especially preferably NaOH. Said fatty acid chlorides are preferably lauroyl chloride.

In a further preferred embodiment of the method according to the invention, fatty acid chlorides $R^1Cl$, in which $R^1$ is an acyl group having 12 carbon atoms, and initially fatty acid chlorides $R^1Cl$, in which $R^1$ is an acyl group having 14 carbon atoms, are reacted in the presence of a basic alkali metal compound which provides cations $Q^+$ selected from $Li^+$, $Na^+$ and $K^+$, preferably selected from $Na^+$ and $K^+$ and particularly preferably $Na^+$. The basic alkali metal compounds are preferably carbonates or hydroxides, preferably hydroxides, of the alkali metal cations $Li^+$, $Na^+$ or $K^+$ or mixtures thereof, particularly preferably NaOH or KOH and especially preferably NaOH.

The method according to the invention is preferably carried out in such a way that glycine is initially introduced in water in the presence of the basic alkali metal compound, such as, for example NaOH, and the fatty acid chloride is added at from 30 to 35° C. The addition of the fatty acid chloride is preferably effected slowly with stirring.

By means of the method according to the invention, salt-containing glycinate solutions having a higher concentration and a low content of byproducts (such as, for example, fatty acid salt) can be prepared, which solutions have a low viscosity and accordingly are easy to handle and moreover are cost-effective since no separation step has to be carried out. Moreover, there is no need for any organic reaction solvent which has to be separated off again and, if appropriate, disposed of.

The invention furthermore therefore relates to compositions containing
a) one or more acylglycinates of the formula (I)

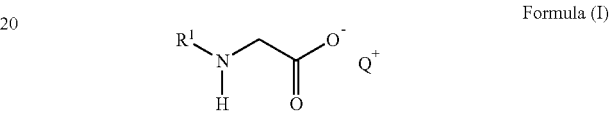

Formula (I)

in which
$R^1$ is a linear or branched, saturated alkanoyl group having 6 to 30, preferably 8 to 22 and particularly preferably 8 to 18 carbon atoms or is a linear or branched, mono- or polyunsaturated alkenoyl group having 6 to 30, preferably 8 to 22 and particularly preferably 12 to 18 carbon atoms, and
$Q^+$ is a cation selected from the alkali metal cations $Li^+$, $Na^+$ and $K^+$, preferably selected from $Na^+$ and $K^+$ and particularly preferably is $Na^+$, in amounts of 21.0-28.0% by weight, based on the total composition, the proportion of acylglycinates of the formula (I) containing acyl groups $R^1$ having 18 or more carbon atoms, based on the total amount of acylglycinates of the formula (I), being less than 2.0, preferably less than 1.8, % by weight,
b) one or more substances $Q^+Cl^-$, in which $Q^+$ has the meaning of $Q^+$ from formula (I), in amounts greater than or equal to 1.0% by weight, based on the total composition,
c) one or more fatty acid salts of the formula (II)

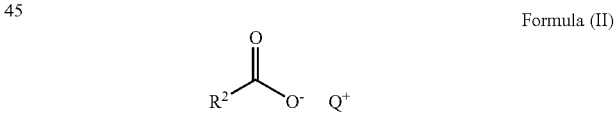

Formula (II)

in which
$R^2CO$ has the meaning of $R^1$ from formula (I) and
$Q^+$ has the meaning of $Q^+$ from formula (I),
in amounts of less than 2.0% by weight, preferably in amounts greater than 0.01% by weight and less than 2.0% by weight and particularly preferably in amounts greater than 0.1% by weight and less than 2.0% by weight, based on the total composition, and
d) water
e) but no organic solvents.
$Q^+Cl^-$ is also designated as QCl, e.g. $Na^+Cl^-$ as NaCl.

In the compounds of the formulae (I) and (II) and in $Q^+Cl^-$, $Q^+$ is selected from $Li^+$, $Na^+$ and $K^+$, preferably selected from $Na^+$ and $K^+$ and particularly preferably $Q^+$ is $Na^+$.

In a preferred embodiment of the invention, the compositions according to the invention contain, as component a), one or more acylglycinates of the formula (I), in which $R^1$ is an acyl group having 8 to 18 carbon atoms and $Q^+$ is a cation selected from $Li^+$, $Na^+$ and $K^+$, preferably selected from $Na^+$ and $K^+$ and particularly preferably is $Na^+$, in amounts of 21.0-28.0% by weight and preferably in amounts of 23.0-27.0% by weight, based on the total composition, the proportion of acylglycinates of the formula (I) containing acyl groups $R^1$ having 18 carbon atoms, based on the total amount of acylglycinates of the formula (I), being less than 2.0, preferably less than 1.8, % by weight.

Compositions containing sodium cocoylglycinate are preferably preferred, the cocoyl cut having only small amounts of $C_{18}$-acyl groups.

In a particularly preferred embodiment of the invention, the compositions according to the invention contain, as component a), sodium cocoylglycinate having $C_{8-18}$-acyl groups in amounts of 21.0-28.0% by weight and preferably in amounts of 23.0-27.0% by weight, based on the total composition, the proportion of acylglycinates of the formula (I) having $C_{18}$-acyl groups being less than 2.0, preferably less than 1.8 and particularly preferably less than 1.0% by weight, based on the total amount of sodium cocoylglycinate. In this embodiment, $Q^+$ in $Q^+Cl^-$ and in the fatty acid salt of the formula (II) is $Na^+$.

In a particularly preferred embodiment of the invention, the compositions according to the invention contain, as component a), sodium cocoylglycinate having $C_{8-18}$-acyl groups being in amounts of 21.0-28.0% by weight and preferably in amounts of 23.0-27.0% by weight, based on the total composition, the proportion of acylglycinates of the formula (I) having $C_8$- and $C_{10}$-acyl groups together being greater than 5.0% by weight preferably from 10.0 to 14.0% by weight, the proportion of acylglycinates of the formula (I) having $C_{12}$-acyl groups being from 50.0 to 72.0% by weight and the proportion of acylglycinates of the formula (I) having $C_{18}$-acyl groups being less than 2.0, preferably less than 1.8 and particularly preferably less than 1.0% by weight, based in each case on the total amount of sodium cocoylglycinate. In this embodiment, $Q^+$ in $Q^+Cl^-$ and in the fatty acid salt of the formula (II) is $Na^+$.

In an extremely preferred embodiment of the invention, the purity of the sodium cocoylglycinates present in the compositions according to the invention is 97% or greater. This purity is based on the sum of fatty acid salt of the formula (II) and acylglycinate of the formula (I). It is calculated according to the formula "purity of sodium cocoylglycinates=[amount of sodium cocoylglycinate: (amount of sodium cocoylglycinate+amount of fatty acid salt)]".

In a further preferred embodiment of the invention, the compositions according to the invention contain, as component a), one or more acylglycinates of the formula (I), in which $R^1$ is an acyl group having 12 carbon atoms and $Q^+$ is a cation selected from $Li^+$, $Na^+$ and $K^+$, preferably selected from $Na^+$ and $K^+$ and particularly preferably is $Na^+$, in amounts of 21.0-28.0% by weight and preferably in amounts of 23.0-27.0% by weight, based on the total composition. Among these acylglycinates of the formula (I) in turn, those in which the acyl group is derived lauroyl chloride are preferred.

In a further preferred embodiment of the invention, the compositions according to the invention contain, as component a), one or more acylglycinates of the formula (I), in which $R^1$ is an acyl group having 12 carbon atoms, and additionally one or more acylglycinates of the formula (I), in which $R^1$ is an acyl group having 14 carbon atoms, and $Q^+$ in each case is a cation selected from $Li^+$, $Na^+$ and $K^+$, preferably selected from $Na^+$ and $K^+$ and particularly preferably is $Na^+$, together in amounts of 21.0-28.0% by weight and preferably in amounts of 23.0-27.0% by weight, based on the total composition.

The compositions according to the invention can, for example, advantageously be used for cosmetic applications.

For cosmetic applications, it is very advantageous if the compositions according to the invention contain $Q^+Cl^-$ in amounts of from 1.0 to 8.0% by weight, so that the separate addition of $Q^+Cl^-$ as a viscosity regulator in the end formulations can be dispensed with.

In a further preferred embodiment of the invention, the compositions according to the invention therefore contain from 1.0 to 8.0, preferably from 2.0 to 7.0 and particularly preferably from 4.0 to 6.0% by weight of $Q^+Cl^-$, based on the total composition.

A further advantage of the compositions according to the invention is that they contain only small amounts of fatty acid salt.

In a further preferred embodiment of the invention, the compositions according to the invention therefore contain less than 1.8, preferably less than 1.5 and particularly preferably less than 1.0% by weight of fatty acid salt of the formula (II), based on the total composition. The lower limit is preferably in each case greater than 0.01% by weight and particularly preferably in each case greater than 0.1% by weight, based on the total composition.

The compositions according to the invention are liquid.

The relatively low viscosity and hence the easy handling of the compositions according to the invention are also very advantageous.

In a further preferred embodiment of the invention, the compositions according to the invention have viscosities at 35° C. of less than 5000 mPa·s, preferably from 400 to 2000 mPa·s and particularly preferably from 500 to 1000 mPa·s.

The apparatus used for determining viscosity is a rotameter from Thermo Haake (Viscotester 550). The spindle used was MV-DIN (45.3 revolutions/minute).

The compositions according to the invention contain no organic solvents, such as, for example lower alcohols, diols or other solvents.

In a particularly preferred embodiment of the invention, the compositions according to the invention consist of the components a), b), c) and d).

In a further particularly preferred embodiment of the invention, the compositions according to the invention consist of the components a), b), c), d) and $H_2NCH_2COO^- Q^+$, in which $Q^+$ is a cation selected from $Li^+$, $Na^+$ and $K^+$, preferably selected from $Na^+$ and $K^+$, and is particularly preferably $Na^+$. In this composition according to the invention, the compound $H_2NCH_2COO^- Q^+$ is preferably present in an amount of from 0.01 to 1.0, and particularly preferably from 0.05 to 0.5% by weight, based on the total composition according to the invention.

The invention furthermore relates to the preparation of the compositions according to the invention by the method according to the invention.

The compositions according to the invention are advantageously suitable for the preparation of cosmetic formulations.

The invention therefore furthermore relates to the use of the compositions according to the invention for the preparation of a cosmetic formulation. It is particularly advantageous that the compositions according to the invention, can be used as obtained from the method according to the invention, i.e. without further working-up or purification.

The compositions according to the invention are moreover advantageously suitable as surfactants in cosmetic formulations.

The invention therefore furthermore relates to the use of the compositions according to the invention as surfactants in cosmetic formulations. Here too, the compositions according to the invention can be used directly as obtained from the method according to the invention.

The following examples and applications are intended to illustrate the invention in more detail but without limiting it thereto. All stated percentages are percent by weight (% by weight).

Cocoyl chloride (A): Coco cut having a reduced proportion of $C_{16}$ and $C_{18}$ Specification of the Cocoyl Chloride Used $C_8/C_{10}$: 10.0-14.0%
$C_{12}$: 60.0-62.0%
$C_{14}$: 19.0-24.0%
$C_{16}$: 3.0-10.0%
$C_{18}$: <2.0%

EXAMPLE 1

37.8 g (0.504 mol) of glycine is dissolved in 276 g of demineralized water with stirring and the pH (telquel) is adjusted to 12-13 with sodium hydroxide solution (33%), Thereafter, heating is effected to 30-35° C. with stirring and 106.4 g (0.478 mol) of cocoyl chloride (A) is metered in in the course of 6 hours at 30-35° C. with cooling of the reaction mixture. The pH is kept at 12-13 by simultaneous metering of sodium hydroxide solution (33%). Toward the end of the metering of the cocoyl chloride, the pH is allowed to decrease to 9.5-10.5. For completing the reaction, stirring is effected for a further 2 hours at pH 9.5-10.5.

The product obtained has the following properties: liquid, opal, residue on drying (1 h, 140° C.): 31.0%, glycine salt (HPLC): 0.6%, fatty acid salt (HPLC): 0.6%, viscosity (35° C.): 756 mPa·s, NaCl (titration): 5.3%, active content: 24.5%

The calculation of the amount by weight of acylglycinate in the compositions according to the invention is effected by means of the formula "amount by weight of acylglycinate=residue on drying−fatty acid salt−glycine salt−$Q^+Cl^-$". In the present invention, the value is designated as "active content".

COMPARATIVE EXAMPLE 2

Higher Reaction Temperature 37.8 g (0.504 mop of glycine is dissolved in 276 g of demineralized water with stirring and the pH (telquel) is adjusted to 12-13 with sodium hydroxide solution (33%). Thereafter, heating to 45-50° C. is effected with stirring and 106.4 g (0.478 mol) of cocoyl chloride (A) is metered in in the course of 6 hours at 45-50° C. The pH is kept at 12-13 by simultaneous metering of sodium hydroxide solution (33%). After about ⅙ of the dose of the cocoyl chloride, the batch is stopped since the calculated amount of sodium hydroxide solution (33%) of the total batch has already been consumed.

The batch has two phases (fatty acid salt). The increased temperature leads predominantly to hydrolysis of the cocoyl chloride.

COMPARATIVE EXAMPLE 3

Lower Reaction Temperature 37.8 g (0.504 mol) of glycine is dissolved in 276 g of demineralized water with stirring and the pH (telquel) is adjusted to 12-13 with sodium hydroxide solution (33%). Thereafter, heating is effected to 25-30° C. with stirring and 106.4 g (0.478 mol) of cocoyl chloride (A) is metered in in the course of 6 hours at 25-30° C. with cooling of the reaction mixture. The pH is kept at 12-13 by simultaneous metering of sodium hydroxide solution (33%). Toward the end of the metering of the cocoyl chloride, the pH is allowed to decrease to 9.5-10.5. For completing the reaction, stirring is effected for a further 2 hours at pH 9.5-10.5.

The product obtained has the following properties: liquid, turbid, residue on drying (1 h, 140° C.): 30.9%, glycine salt (HPLC): 1.3%, fatty acid salt (HPLC): 2.4%, viscosity: not determined, NaCl (titration): 5.3%, active content: 21.9%

EXAMPLE 4

Higher Glycine Excess 37.8 g (0.504 mol) of glycine is dissolved in 250 g of demineralized water with stirring and the pH (telquel) is adjusted to 12-13 with sodium hydroxide solution (33%). Thereafter, heating is effected to 30-35° C. with stirring and 95.2 g (0.428 mol) of cocoyl chloride (A) is metered in in the course of 6 hours at 30-35° C. with cooling of the reaction mixture. The pH is kept at 12-13 by simultaneous metering of sodium hydroxide solution (33%). Toward the end of the metering of the cocoyl chloride, the pH is allowed to decrease to 9.5-10.5. For completing the reaction, stirring is effected for a further 2 hours at pH 9.5-10.5.

The product obtained has the following properties: liquid, opal, residue on drying (1 h, 140° C.): 31.3%, glycine salt (HPLC): 1.3%, fatty acid salt (HPLC): 0.2%, viscosity (35° C.): 980 mPa·s, NaCl (titration): 5.1%, active content: 24.7%

EXAMPLE 5

Higher Concentration 37.8 g (0.504 mol) of glycine is dissolved in 246 g of demineralized water with stirring and the pH (telquel) is adjusted to 12-13 with sodium hydroxide solution (33%). Thereafter, heating is effected to 30-35° C. with stirring and 106.4 g (0.478 mol) of cocoyl chloride (A) is metered in in the course of 6 hours at 30-35° C. with cooling of the reaction mixture. The pH is kept at 12-13 by simultaneous metering of sodium hydroxide solution (33%). Toward the end of the metering of the cocoyl chloride, the pH is allowed to decrease to 9.5-10.5. For completing the reaction, stirring is effected for a further 2 hours at pH 9.5-10.5.

The product obtained has the following properties: liquid, opal, residue on drying (1 h, 140° C.): 32.7%, glycine salt (HPLC): 0.8%, fatty acid salt (HPLC): 1.3%, viscosity (35° C.): 4500 mPa·s, NaCl (titration): 5.6%, active content: 25.0%

COMPARATIVE EXAMPLE 6

Salt-Free Preparation in 2-Propanol/Water 94.5 g (1.26 mol) of glycine is dissolved in 400 g of demineralized water and 276 g of 2-propanol with stirring and the pH (telquel) is adjusted to 12-13 with sodium hydroxide solution (33%). Thereafter, 283.9 g (1.24 mol) of cocoyl chloride (A) are metered in in the course of 6 hours with stirring at 25-27° C. with cooling of the reaction mixture. The pH is kept at 12-13 by simultaneous metering of sodium hydroxide solution (33%). To complete the reaction, stirring is effected for a further 2 hours at pH 12-13. The product obtained is adjusted to pH 1 with concentrated hydrochloric acid. After the stirrer has been switched off, the phase separation begins immediately. The aqueous phase is separated off and the organic phase is adjusted to pH 4.6 with sodium hydroxide solution (33%). After addition of 740 g of water, the pH is adjusted to 7.0 with sodium hydroxide solution (33%). Thereafter, 2-propanal/water is distilled off at reduced pressure (about 140-160 mbar) and 55° C. until the 2-propanol content in the product has fallen below 1%. With the aid of water and sodium hydroxide solution, a solids content of 30% and a pH of 10.0 are established.

The product has the following properties: liquid, clear, residue on drying (1 h, 140° C.): 30.3%, glycine salt (HPLC): <0.1%, fatty acid salt (HPLC): 1.0%, 2-propanol (GC): <0.1%, chloride (titration): 0.35%, viscosity: not determined, NaCl (titration): 0.6%, active content: 28.7%

COMPARATIVE EXAMPLE 7

Coco Cut Having Increased Proportion of $C_{16/18}$, Hydrogenated

Distribution of the cocoyl chloride (B) used:
$C_{12}$: 55.6%
$C_{14}$: 23.0%
$C_{16}$: 11.1%
$C_{18}$ saturated: 10.3%

36.0 g (0.480 mol) of glycine is dissolved in 280 g of demineralized water with stirring and the pH (telquel) is adjusted to 12-13 with sodium hydroxide solution (33%). Thereafter, heating to 30-35° C. is effected with stirring and 109.6 g (0.456 mol) of cocoyl chloride (B) is metered in in the course of 6 hours at 30-35° C. with cooling of the reaction mixture. The pH is kept at 12-13 by simultaneous metering of sodium hydroxide solution (33%). In the course of the metering of the cocoyl chloride, the batch becomes increasingly viscous until it is no longer stirrable. By addition of 110 g of water and subsequent increase of the reaction temperature to 40° C., the batch remains reasonably stirrable. Toward the end of the metering of the cocoyl chloride, the pH is allowed to fall to 9.5-10.5. To complete the reaction, stirring is effected for a further 2 hours at pH 9.5-10.5.

The product obtained has the following properties: liquid, turbid, residue on drying (1 h, 140° C.): 25.8%, glycine salt (HPLC): 0.8%, fatty acid salt (HPLC): 1.2%, viscosity: not determined, NaCl (titration): 4.1%, active content: 19.7%

The examples described show that highly concentrated alkali metal salt glycinate solutions having an active content >22.0%, preferably >23.0% and particularly preferably >24.0% can be obtained by use of a low-$C_{18}$ coconut fatty acid cut and reaction in water without additional solvents at 30-35° C. (example 1, example 4, example 5). In example 1, it was possible to achieve a purity of the glycinate solution of 97.6% of acylglycinate, based on the sum of fatty acid salt and acylglycinate. On the other hand, higher reaction temperatures (comparative example 2) lead to greatly increased fatty acid salt contents. Lower reaction temperatures (comparative example 3) likewise lead to undesirably high proportions of fatty acid salts. With the use of $C_{16}/C_{18}$-rich fatty acid chlorides (comparative example 7), undesirably low active contents are obtained.

The invention claimed is:
1. A method for producing an acylglycinate of the formula (I)

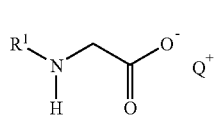

Formula (I)

wherein
  $R^1$ is a linear or branched, saturated alkanoyl group having 8 to 18 carbon atoms or is a linear or branched, mono- or polyunsaturated alkenoyl group having 8 to 18 carbon atoms, and
  $Q^+$ is a cation selected from the alkali metal cations $Li^+$, $Na^+$ and $K^+$,
  wherein glycine is reacted with $C_8$-$C_{18}$cocoylchloride in water and in the presence of a basic alkali metal compound which provides cations $Q^+$, but in the absence of organic solvents, at 30-35° C., and wherein the proportion of $C_8$-$C_{18}$cocoylchloride having 18 carbon atoms, based on the total amount of $C_8$-$C_{18}$cocoylchloride used, is less than 2.0% by weight.

2. A method as claimed in claim 1, wherein carbonates or hydroxides, of the alkali metal cations $Li^+$, $Na^+$ or $K^+$ or mixtures thereof are used as basic alkali metal compounds.

3. A method as claimed in claim 1, carried out at a pH of from 9 to 13.

4. A method as claimed in claim 1, wherein the molar ratio of glycine to $C_8$-$C_{18}$cocoylchloride is from 1.1:1.0 to 1.0:1.0.

5. A method as claimed in claim 1, wherein the cocoylchloride used has been obtained by distillation from a customary cocoylchloride.

6. A composition containing
  a) at least one acylglycinate of the formula (I)

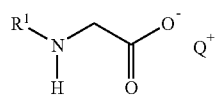

Formula (I)

wherein
  $R^1$ is a linear or branched, saturated alkanoyl group having 8 to 18 carbon atoms, or is a linear or branched, mono- or polyunsaturated alkenoyl group having 8 to 18 carbon atoms, and
  $Q^+$ is $Na^+$,
  wherein the at least one acylglycinate of component a) is sodium cocoylglycinate with $C_8$-$C_{18}$ acyl groups in amounts of 21.0-28.0% by weight, based on the total composition,
  wherein the proportion of sodium cocoylglycinate with $C_{18}$ acyl groups, is less than 2% by weight based on the total amount of sodium cocoylglycinate,
  b) at least one substance $Q^+Cl^-$, in which $Q^+$ is defined above, in amounts greater than or equal to 1.0% by weight, based on the total composition,
  c) at least one fatty acid salt of the formula (II)

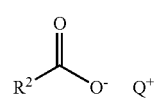

Formula (II)

wherein
  $R^2CO$ is defined as $R^1$ from formula (I) and $Q^+$ is defined as $Q^+$ from formula (I), in amounts of less than 2.0% by weight, based on the total composition, and d) water wherein the composition contains no organic solvents.

7. A composition as claimed in claim 6, containing 21.0-28.0% of component a) by weight based on the total composition, wherein component a) is sodium cocoylglycinate having $C_{8-18}$-acyl groups the proportion of the sodium cocoylglycinate having $C_8$- and $C_{10}$-acyl groups is greater than 5.0% by weight of the sodium cocoylglycinate, the proportion of the sodium cocoylglycinate having $C_{12}$-acyl groups being is from 50.0 to 72.0% by weight of the sodium cocoylglycinate, and the proportion of the sodium cocoylglycinate, having $C_{18}$-acyl groups is less than 2.0% by weight of the sodium cocoylglycinate.

8. A composition as claimed in claim 6, wherein it contains, based on the total composition, from 1.0 to 8.0% by weight of $Q^+Cl^-$.

9. A composition as claimed in claim 6, wherein it contains, based on the total composition, less than 1.8% by weight of the at least one fatty acid salt of the formula (II).

10. A composition as claimed in claim 6, wherein it has a viscosity at 35° C. of less than 5000 mPa.s.

11. A cosmetic formulation comprising at least one composition as claimed in claim 6.

12. A cosmetic formulation comprising a composition as claimed in claim 6 as a surfactant.

\* \* \* \* \*

(12) EX PARTE REEXAMINATION CERTIFICATE (10558th)
United States Patent
Klug et al.

(10) Number: US 8,338,483 C1
(45) Certificate Issued: Mar. 31, 2015

(54) METHOD FOR PRODUCING ACYLGLYCINATES

(75) Inventors: Peter Klug, Grossostheim (DE); Franz-Xaver Scherl, Burgkirchen (DE)

(73) Assignee: Clariant Finance (BVI) Limited, Tortola, Virgin Islands (VG)

Reexamination Request:
No. 90/013,244, May 29, 2014

Reexamination Certificate for:
Patent No.: 8,338,483
Issued: Dec. 25, 2012
Appl. No.: 12/743,458
PCT Filed: Nov. 14, 2008
PCT No.: PCT/EP2008/009646
§ 371 (c)(1),
(2), (4) Date: May 28, 2010
PCT Pub. No.: WO2009/065530
PCT Pub. Date: May 28, 2009

(30) Foreign Application Priority Data

Nov. 20, 2007  (DE) .......................... 10 2007 055 265

(51) Int. Cl.
| | | |
|---|---|---|
| *A61K 31/198* | (2006.01) | |
| *A61Q 19/00* | (2006.01) | |
| *A61K 8/44* | (2006.01) | |
| *C07C 231/02* | (2006.01) | |
| *C07C 233/47* | (2006.01) | |

(52) U.S. Cl.
CPC . *A61Q 19/00* (2013.01); *A61K 8/44* (2013.01); *C07C 231/02* (2013.01); *C07C 233/47* (2013.01)
USPC .......................................... 514/563; 554/110

(58) Field of Classification Search
None
See application file for complete search history.

(56) References Cited

To view the complete listing of prior art documents cited during the proceeding for Reexamination Control Number 90/013,244, please refer to the USPTO's public Patent Application Information Retrieval (PAIR) system under the Display References tab.

*Primary Examiner* — Alan Diamond

(57) ABSTRACT

The invention relates to a method for producing acylglycinates of formula (I)

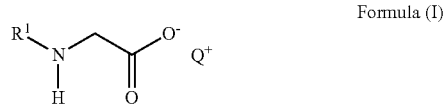

Formula (I)

wherein $R^1$ represents a linear or branched, saturated alkanoyl group having between 6 and 30 carbon atoms, or a linear or branched, mono- or polyunsaturated alkenoyl group having between 6 and 30 carbon atoms, and $Q^+$ represents a cation selected from the alkali metals $Li^+$, $Na^+$ and $K^+$, characterised in that glycine comprises fatty acid chloride $R^1Cl$, wherein $R^1$ which has the meaning given in formula (I), is provided in water and in presence of a basic alkali compound, the cations $Q^+$ are selected from $Li^+$, $Na^+$ and $K^+$, but in the absence of organic solvents, is reacted at between 30-35 DEG C, and the proportion of fatty acid chloride $R^1Cl$ containing acyl groups $R^1$ having 18 or more carbon atoms, in relation to the total amount of used fatty acid chloride, is less than 2.0% in wt.

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1-12 are cancelled.

\* \* \* \* \*